Figure 4:
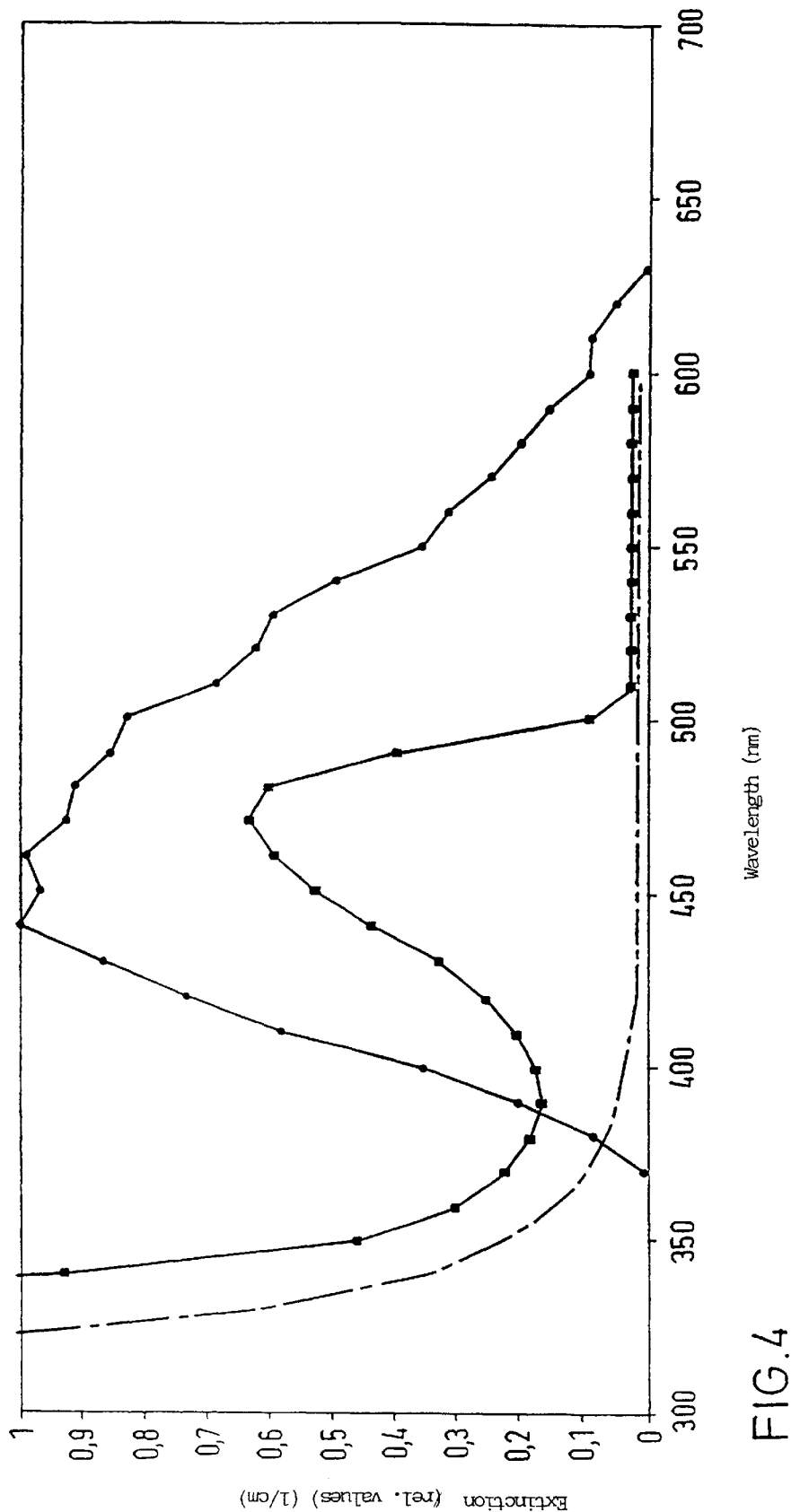

United States Patent [19]
Rechmann

[11] Patent Number: 6,065,965
[45] Date of Patent: May 23, 2000

[54] DEVICE AND PROCESS FOR CURING A PHOTOCURABLE PLASTIC FILLER

[76] Inventor: Peter Rechmann, Dellestrasse 79, 40627 Duesseldorf-Unterbach, Germany

[21] Appl. No.: 09/155,764
[22] PCT Filed: Jan. 31, 1998
[86] PCT No.: PCT/EP97/00430
§ 371 Date: Oct. 5, 1998
§ 102(e) Date: Oct. 5, 1998
[87] PCT Pub. No.: WO97/37611
PCT Pub. Date: Oct. 16, 1997

[30] Foreign Application Priority Data

Apr. 4, 1996 [DE] Germany ............... 196 13 566

[51] Int. Cl.⁷ ............... A61C 1/00; A61C 3/00; A61C 5/04
[52] U.S. Cl. ............... 433/29; 433/226
[58] Field of Search ............... 433/29, 215, 226, 433/229, 90

[56] References Cited

U.S. PATENT DOCUMENTS

| | | | |
|---|---|---|---|
| 4,957,441 | 9/1990 | Bryan | 433/226 X |
| 5,007,837 | 4/1991 | Werly | 433/226 |
| 5,171,150 | 12/1992 | Levy | 433/226 |
| 5,695,340 | 12/1997 | Lee et al. | 433/226 |
| 5,788,499 | 8/1998 | Hoffman | 433/226 |

*Primary Examiner*—Nicholas D. Lucchesi
*Attorney, Agent, or Firm*—Diller, Ramik & Wight, PC

[57] ABSTRACT

A deice for curing a photocurable plastic filler (6) disposed in a dental cavity (2) of a hard tooth substance (4) includes a laser light source (10) and a light conductor (11) leading from the laser light source (10) to an applicator (14). The applicator (14) is utilized to apply drops of the plastic filler (6) upon the dental cavity alternating with an intermittent operation of the laser light source (10).

28 Claims, 2 Drawing Sheets

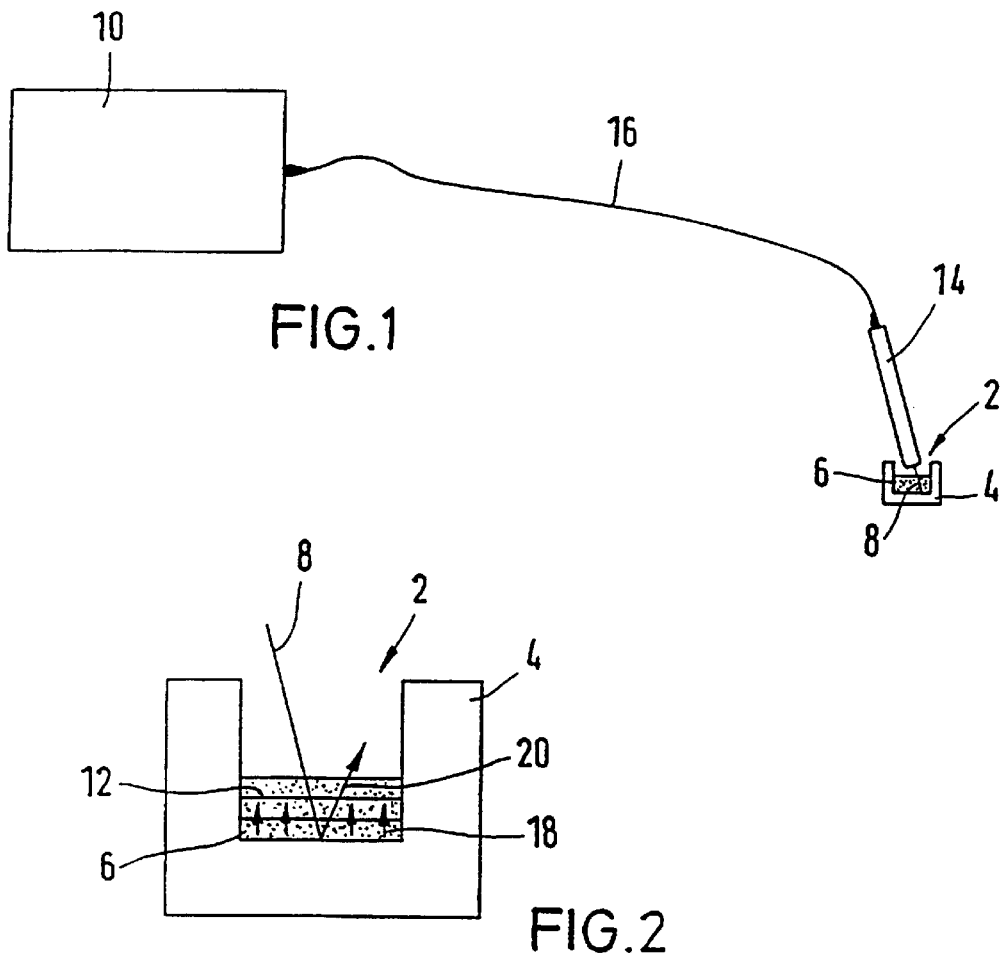
FIG.1
FIG.2
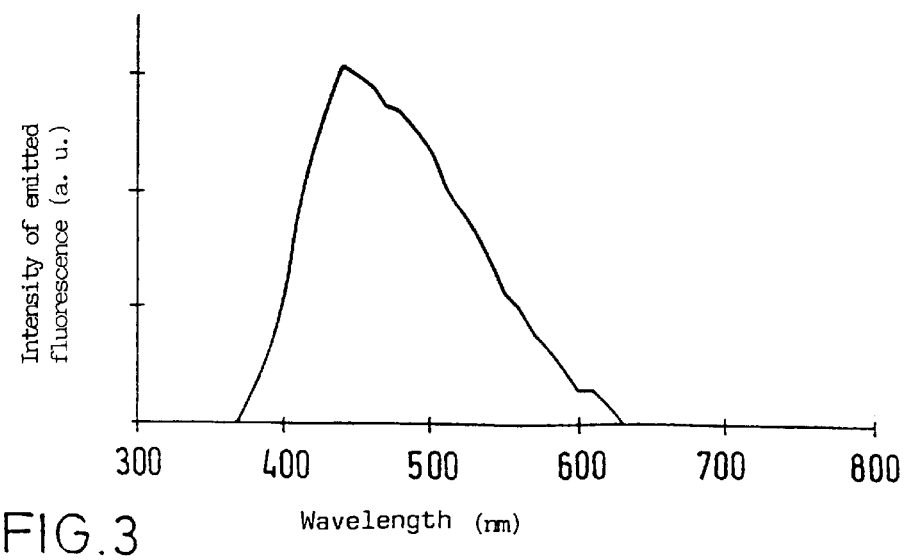
FIG.3

DEVICE AND PROCESS FOR CURING A PHOTOCURABLE PLASTIC FILLER

The invention relates to a device and a process for curing a photocurable filler, e.g. a plastics or composite material.

As a replacement for amalgam, such plastic fillers are introduced into the tooth cavity in a more or less viscous state and will cure there subsequently. The polymerization may be initiated with light, if a corresponding photo-initiator has been added to the filler. The fillers are cured by photopolymerization. The polymerization of dental plastics materials for tooth cavities is effected using blue light, e.g. with a wavelength from 420 to 470 nm, that is, within the range of the maximum absorption of an initiator used in the plastic filler, such as camphor-chinon. The shrinking entailed by the polymerization causes the forming of edge gaps at the edge of the tooth cavity and tensions within the filler by the build-up of internal tensions. These tensions will result in a loss of the tight sealing of the tooth cavity, especially under load. Via the edge gaps, bacteria may enter deep into the tooth cavity where they again foster cariogenicity.

It is another problem of photopolymerization that the filler always polymerizes in the direction of the curing light source. The first areas to polymerize are the ones closest to the light source. Therefore, plastic fillers typically polymerize last at the borders of the tooth cavity. This causes substantial tension forces at the interface between the hard tooth substance and the plastics material. The tension becomes more complex as the the walls of a tooth cavity increase.

It has been attempted to ameliorate the problem occurring during photopolymerization by arranging the light source laterally so that the polymerizing light radiates through the tooth, thereby to effect a polymerization starting from the edge of the tooth cavity.

Conventional photopolymerization light sources with wavelengths between 400 and 500 nm and a power density of <200 mW/cm$^2$, however, are very much attenuated when radiating through dentine and the outer enamel layer of the tooth. Thus, this method can be used only for very thin dentine/enamel walls. With larger wall thicknesses, the plastic filler cannot be cured.

It has been suggested to use an argon laser with a wavelength of 488 mn as the light source for the polymerization of the plastic material. Such a laser has a wavelength within the maximum absorption range of the photo-initiator so that this type of laser is no different from conventional polymerization light sources, except for the radiation intensity. The laser light is largely absorbed in the plastic filler, which is why it has a small penetration depth and the disadvantage of edge gap formation.

It is an object of the present invention to provide a device for and a process of curing a photocurable plastic filler with which the build-up of tension during polymerization shrinking can be substantially reduced.

The object is solved with the features of claims 1 and 8, respectively.

The invention advantageously provides for successively introducing small amounts of plastic filler into the tooth cavity and for curing these, respectively. Preferably, these amounts of plastic filler that spread to form thin layers, are injected into the tooth cavity through a separate applicator or the laser light applicator, whereupon they are immediately polymerized by the application of laser light.

Laser light irradiation causes an improved cross-linking of the plastic filler material due to the higher power density of the laser light as compared with conventional polymerization light sources, and thereby causes improved material properties. Until now, this improved cross-linking could only be achieved experimentally during extra-oral additional polymerization and was thus not suited for practical use. An improved cross-linking causes a reduction of the free or releasable monomers of the plastic filler. This goes together with a reduction in the toxicity of the plastic filler.

A laser light source is used having a laser light beam of a wavelength that is only weakly absorbed by the plastic filler and is below the maximum absorption of the initiator used in the plastic filler. Such a laser light beam is hardly absorbed by the plastic filler so that the laser light beam radiates through the plastic filler onto the hard tooth substance defining the tooth cavity. The laser light beam is partly reflected from the hard tooth substance and is partly used to cause the hard tooth substance to emit fluorescent radiation. The emitted fluorescent radiation is within a wavelength range that corresponds to the maximum absorption of the initiator in the plastic filler. Exciting the emission of a fluorescent radiation results in the curing of the plastic filler to start from the walls of the tooth cavity, i.e., the curing is directed towards the tooth surface and not the light source.

The polymerization by the fluorescent light is partly overlapped by the substantially reduced direct polymerization by the laser light beam and the reflected part thereof that also results in a polymerization towards the surface of the tooth (similar to the fluorescent light). In the end, this results in a substantial decrease in tension so that no edge gaps are formed.

This procedure is particularly advantageous when anchoring the first thin plastic filler layers in the hard tooth substance. With the layer thickness or the distance of the hard tooth substance increasing, the polymerization is increasingly effected directly with the laser light beam corresponding to the residual absorption by the plastic filler.

A laser light beam with a wavelength in the range from 350 to 440 nm, preferably 460 to 425 nm, is used. Particular preference is given to a wavelength range between 370 and 410 nm.

The emitted fluorescent radiation of the hard tooth substance occurs in a wavelength range between approximately 400 to 600 nm. Thus, the emitted fluorescent radiation is exactly in the range of the maximum absorption of the initiator in the plastic filler.

It may be provided to ad a fluorescent filler material, such as ceramics, to the plastic filler.

Preferably, a pulsed or chopped laser light beam is used. It is also possible to use a continuous laser light beam.

The plastic material is applied intermittently. Besides a pneumatic application, one may also utilize mechanical or electro mechanical application of the non-cured filler.

The plastic filler layers may be introduced by means an oxygen-free propellant gas.

Using an oxygen-free propellant leads to a better quality of the plastic filling.

When pulsed laser light is used, an energy density of the laser light beam of less than 2 J/cm$^2$, preferably less than 1.5 J/cm$^2$, is used to cure the plastic filler.

To remove smear layers, the laser light may be applied with a higher energy density. Thus, it is also possible, without having to change the applicator instrument, to remove smear layers prior to introducing the plastic filler.

The following is a detailed description of an embodiment of the invention with reference to the drawings.

In the Figures:

FIG. 1 illustrates the device for curing a photocurable plastic filler according to the present invention, FIG. 2 is an enlarged illustration of a tooth cavity partly filled with several layers of plastic filler, FIG. 3 illustrates the emission intensity of the fluorescent light for dentine when excited by laser light, and FIG. 4 shows the light extinction of the plastic material with and without an initiator and the relative emission of fluorescence of the hard tooth substance as a function of the wavelength.

Referring to FIG. 1, the device for curing a plastic filler, such as a plastic composite material, for dental fillings comprises a laser light source 10 and a flexible light conductor 16 leading the laser light from the laser light source 10 to an applicator 14. Using the applicator 14, the laser light beam 8 may be directed onto a dental cavity in the hard tooth substance 4 of a tooth. Within the dental cavity 2, there is a photocurable plastic filler 6, preferably introduced into the dental cavity 2 in small amounts spreading into thin layers 12, the filler being cured immediately thereafter in a layer by layer manner using the laser light beam 8.

The plastic filler 6 is a conventional photopolymerizable plastic material that may include a high percentage of an inorganic filling agent. It is also known to add glass particles of different sizes to the plastic filler in order to reduce curing contractions and abrasion.

It is essential to introduce the plastic filler 6 into the dental cavity 2 as thin layers 12 of plastic filler and to cure these immediately after introduction in a layer by layer manner. This incremental procedure allows for a largely tension-free curing of the individual plastic filler layers 12 so that eventually the entire dental filling can be built tension-free. The non-cured plastic material may be introduced without filling agents using a nozzle arranged in an applicator, provided separately, if need be, the filling agents being simultaneously or alternately introduced into the cavity using a second nozzle. One may also provide two nozzles for the plastic filler should a two-component material be used.

The plastic filler 6 is introduced dropwise into the dental cavity 2 by means of the laser light applicator 14 or by means of a separate applicator and is immediately cured using the laser light intermittently switched on in alternately with the injection of plastic material. Thus, in constant succession, a drop of plastic material is injected that spreads into a thin plastic filler layer 12 in the dental cavity 2 and is immediately afterwards cured by the laser light. Such a plastic filler injection and curing cycle may be carried out with a high repetition rate of, e.g., 20 Hz, whereby a fast incremental multi-layer filling can be achieved and the plastic filler 6 can be cured bubble-free.

FIG. 2 is a schematic illustration of a dental cavity 2 in a hard tooth substance 4. Several layers 12 of plastic filler are arranged on top of each other in the dental cavity 2. The incident laser light beam is reflected at the bottom of the dental cavity 2 so that the reflected laser light beam 20 can again penetrate the plastic filler layers 12 with reduced intensity. A part of the energy introduced with the laser light beam 8 is used to excite the hard tooth substance 4 to emit fluorescent light beams 18 that start from the walls of the dental cavity 2 and contribute the major part to the curing of the plastic filler 6 due to their wavelength range between 400 and 600 nm.

FIG. 3 shows the intensity of the emitted fluorescent light of the hard tooth substance 4 excited by a nitrogen laser (337 nm) as a function of the wavelength.

FIG. 4 illustrates the extinction behavior of the plastic filler material as a function of the wavelength. The lowermost curve without any particular maximum represents the pure plastic material without initiator. The central curve with a strong maximum at about 470 nm is the actual measured extinction of the plastic filler with an initiator (camphorchinon) present. The third curve, having a maximum between 430 and 460 run, represents the wavelength of the emitted fluorescence. Typically such plastic fillers are cured using photopolymerization devices operating in a wavelength range between 400 and 500 nm, that is in the maximum range of the absorption peak caused by the photo-initiator.

Yet, with the device described, it is possible to use laser light with a wavelength in the range between 350 to 440 nm, preferably in the range between 370 and 410 nm. As can be seen in FIG. 4, laser light of this wavelength is subjected to minimum absorption in this region in the plastic filler 6 so that the laser light is absorbed to a lesser extent while having a greater penetration depth. Thus, the laser light penetrates the plastic filler layers 12 to hit the hard tooth substance where a part of the laser light beam 8 is reflected, whereas the other part excites the hard tooth substance to emit fluorescent light. This fluorescent light radiation 18 is within a wavelength range between 400 and 600 nm, that is within the range of the maximum absorption of the plastic filler material 6. As a result, in particular the first plastic filler layer establishes a particularly firm bond with the hard tooth substance 4 since, in this instance, the polymerization is effected predominantly by the emitted fluorescent light and not by the direct irradiation of laser light. Thus, the curing of the plastic filler layer 12 starts from the tooth and continues towards the surface of the filling. This curing from the walls of the dental cavity 2 outward causes, as earlier mentioned, an extremely good adherence of the first plastic filler layer 12 on the hard tooth substance 4 and avoids the previously mentioned problems of great tension forces with the accompanying formation of edge gaps.

Up to a certain layer thickness, the further plastic filler layers 12 are also very well penetrated by the laser light beam 8 so that the positive effect of the emitted fluorescent beams may be used up to a certain depth of the plastic filler layers 12. In any case, the emitted fluorescent radiation has a positive effect in the area of the walls of the dental cavity 2, even with deeper dental cavities 2. The curing of the plastic filler 6 towards the borders of the dental cavity eliminates the occurrence of the edge gap problem and further substantially reduces the tensions building during the curing. Moreover, as earlier mentioned, tensions are also reduced by applying thin layers 12 of plastic filler so that there is no large shrinking volume.

With larger distances from the hard tooth substance, the efficiency of fluorescent radiation decreases, so that the radiation dose (power or irradiation time) has to be increased.

Instead of the glass particle filling agent described earlier, it is possible to add fluorescent material as a filling agent to the plastic filler 6. This fluorescent filling agent may comprise ceramics particles, for example. The plastic filler 6 with fluorescent filling agent would be advantageous for use in deeper dental cavities 2 in order to achieve a sufficiently high degree of polymerization in all layers of a plastic filling even with low radiation doses.

Applying thin plastic filler layers 12 is advantageous in that the polymerization heat generated by the polymerization reaction is substantially reduced.

Preferably, the laser light used is pulsed, however, a continuous wave laser or chopped lasers may also be used. When a pulsed laser light source is used, an energy density of less than 2 J/cm$^2$, preferably less than 1.5 J/cm$^2$, is required. Using a laser light source, average power densities of more than 1 W/cm² can be achieved. Thereby, short irradiation times are obtained.

Prior to filling the dental cavity 2 with the plastic filler 6, the laser light may also be used to condition the dental cavity 2 in the hard tooth substance 4 without having to change the applicator 14.

Employing an increased power density between about 2 J/cm² and 6 J/cm², the laser beam 8 may be used to remove the smear layer, which is a layer of abraded dentine left after preparing the tooth with a drill. In doing so, all dentine channels are opened wide. The plastic filler 6 can enter these opened channels during the subsequent filling and thereby increase the mechanical adhesion of the filling.

What is claimed is:

1. A device for curing a photocurable plastic filler (6) disposed in a dental cavity (2) of a hard tooth substance (4) comprising a laser light source (10) and a light conductor (16) leading from the laser light source (10) to an applicator (14), the applicator (14) including means for applying drops of the plastic filler (6) upon the dental cavity alternating with means for generating from the laser light source (10) an intermittently operated laser beam (8).

2. The device of claim 1 wherein the laser light source (10) emits a laser light beam (8) with a wavelength in a range between 350 to 440 nm.

3. The device of claim 1 wherein the applicator (14) has two nozzles for applying a two-component plastic filler (6).

4. The device of claim 1 wherein the wavelength of the laser light beam (8) emitted by the laser light source (10) is in the range from about 370 to 410 nm.

5. The device of claim 1 wherein the laser light source (10) is a pulsed laser light source.

6. The device of claim 1 wherein the laser light source (10) is a continuous wave laser.

7. The device of claim 5 wherein the power density of the pulsed laser light source (10) is less than about 2 J/cm².

8. A method of curing a photocurable plastic filler by photopolymerization using a laser light beam (8) comprising the steps of successively and repeatedly applying small amounts (12) of plastic filler (6) upon a dental cavity (2) and immediately curing each small amount (12) after application using an intermittently operated laser light beam (8).

9. The method as defined in claim 8 wherein a laser light source (10) is used to create the laser light beam (8) having a wavelength only weakly absorbed by the plastic filler (6) and lying below the maximum absorption of an initiator used in the plastic filler (6), the laser light beam (8) being partly reflected by a hard tooth substance (4) of the dental cavity (2) underneath the plastic filler (6), and the hard tooth substance (4) being excited by a part of the laser light beam (8) to emit fluorescent radiation (18) in a wavelength range within the range of the maximum absorption of the initiator in the plastic filler (6).

10. The method as defined in claim 8 wherein the laser beam (8) has a wavelength in the range from 350 to 440 nm.

11. The method as defined in claim 8 wherein the laser light beam (8) has a wavelength in the range from 370 to 410 nm.

12. The method as defined in claim 8 wherein the plastic filler (6) is applied in layers.

13. The method as defined in claim 8 wherein the plastic filer (6) includes a fluorescent filling agent.

14. The method as defined in claim 8 wherein the laser light beam (8) is a pulsed laser light beam (8).

15. The method as defined in claim 8 wherein the laser light beam (8) is a continuous laser light beam (8).

16. The method as defined in claim 8 wherein the plastic filler (6) is two components.

17. The method as defined in claim 8 including the step of applying the plastic filler in layers (12) by injection into the dental cavity (2).

18. The method as defined in claim 14 wherein the power density of the laser light pulse used is less than 2 J/cm².

19. The method as defined in claim 8 wherein the laser light beam (8) has an increased power density between 2 J/cm² and 6 J/cm² for removing a smear layer.

20. The method as defined in claim 8 wherein the plastic filler (6) includes an increased initiator percentage of about 2% to 5%.

21. The device of claim 1 wherein the laser light source (10) emits a laser light beam (8) with a wavelength in a range between 360 to 425 nm.

22. The device of claim 1 wherein the laser light source (10) is a chopped laser light source.

23. The device of claim 5 wherein the power density of the chopped laser light source (10) is less than about 2 J/cm².

24. The device of claim 5 wherein the power density of the chopped laser light source (10) is less than about 1.5 J/cm².

25. The device of claim 5 wherein the power density of the chopped laser light source (10) is less than about 1.5 J/cm².

26. The method as defined in claim 8 wherein the laser beam (8) has a wavelength in the range from 360 to 425 nm.

27. The method as defined in claim 8 wherein the laser light beam (8) is a chopped laser light beam (8).

28. The method as defined in claim 14 wherein the power density of the laser light pulse used is less than 1.5 J/cm².

* * * * *

UNITED STATES PATENT AND TRADEMARK OFFICE
CERTIFICATE OF CORRECTION

PATENT NO. : 6,065,965  
DATED : May 23, 2000  
INVENTOR(S) : Peter Rechmann

Page 1 of 1

It is certified that error appears in the above-identified patent and that said Letters Patent is hereby corrected as shown below:

IN THE HEADING:

PCT Filed information should read: -- Jan. 31, 1997 --.

Signed and Sealed this

Eleventh Day of September, 2001

Attest:

NICHOLAS P. GODICI  
*Attesting Officer*  *Acting Director of the United States Patent and Trademark Office*